United States Patent [19]

Evans et al.

[11] Patent Number: 4,575,511

[45] Date of Patent: Mar. 11, 1986

[54] ANTI-HYPERTENSIVE CHROMANOL DERIVATIVES

[75] Inventors: John M. Evans, Roydon; Frederick Cassidy, Harlow, both of England

[73] Assignee: Beecham Group p.l.c., England

[21] Appl. No.: 610,626

[22] Filed: May 16, 1984

[30] Foreign Application Priority Data

May 18, 1983 [GB] United Kingdom ............... 8313676
May 18, 1983 [GB] United Kingdom ............... 8313681
May 18, 1983 [GB] United Kingdom ............... 8313683
May 18, 1983 [GB] United Kingdom ............... 8313688

[51] Int. Cl.[4] .................. A61K 31/35; C07D 311/02
[52] U.S. Cl. ........................... 514/456; 549/404; 549/399; 549/345
[58] Field of Search ............... 549/399, 404, 345; 424/283; 514/456

[56] References Cited

U.S. PATENT DOCUMENTS 4,115,407 9/1978 Wright et al. .................. 549/404
4,363,811 12/1982 Evans et al. ................... 548/525
4,366,163 12/1982 Evans et al. ................... 546/196
4,446,113 5/1984 Evans et al. ................... 424/267
4,481,214 11/1984 Evans ........................... 424/283

FOREIGN PATENT DOCUMENTS 0035868 9/1981 European Pat. Off. .
46652 3/1982 European Pat. Off. ............ 549/399
0095316 11/1983 European Pat. Off. .

OTHER PUBLICATIONS

Lap et al., *Aust. J. Chem.*, 1979, 32 pp. 619–636.

Primary Examiner—Nicky Chan
Attorney, Agent, or Firm—Jacobs & Jacobs

[57] ABSTRACT

Compounds of formula (I):

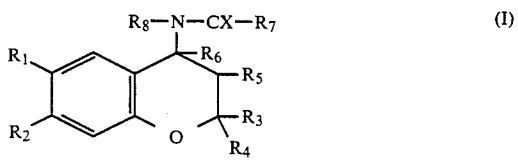

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkoxysulphinylamino, $C_{1-6}$ alkoxysulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is selected from the class consisting of $C_{1-6}$ alkyl substituted by amino optionally substituted by one or two $C_{1-6}$ alkyl groups which may be the same or different; amino optionally substituted by a $C_{1-6}$ alkyl or $C_{1-6}$ alkenyl group or a $C_{1-6}$ alkanoyl group optionally substituted by up to three halo atoms or by a phenyl group optionally substituted by $C_{1-6}$ alkyl, $C_{1-6}$ alkoxy or halogen; or $C_{1-6}$ alkoxy, or phenoxy optionally substituted by $C_{1-6}$ alkyl, $C_{1-6}$ alkoxy or halogen; or, when X is oxygen, $R_7$ is further selected from the class of carboxy, $C_{1-6}$ alkoxycarbonyl, or aminocarbonyl optionally substituted by one or two $C_{1-6}$ alkyl groups which may be the same or different;
$R_8$ is hydrogen or $C_{1-6}$ alkyl; and
X is oxygen or sulphur;
the $R_8$—N—CX—$R_7$ group being trans to the $R_5$ group when $R_5$ and $R_6$ together are not a bond;
or when the compound of formula (I) contains a salifiable group, pharmaceutically acceptable salts thereof, having pharmacological activity, a process for preparing them, pharmaceutical compositions containing them, and their use in the treatment of mammals.

15 Claims, No Drawings

ANTI-HYPERTENSIVE CHROMANOL DERIVATIVES

The present invention relates to novel chromans and chromenes having pharmacological activity, to a process for preparing them, to pharmaceutical compositions containing them, and to their use in the treatment of mammals.

U.S. Pat. Nos. 4,110,347 and 4,119,643 and 4,251,537 and European Patent Publications Nos. 28 064 and 28 449 discloses classes of chromans that are described as having blood pressure lowering activity or anti-hypertensive activity.

European Patent Publication No. 76 075 discloses a further class of chromans that are substituted in the 4-position by a piperidonyl or pyrrolidonyl group. Such chromans are also described as having blood pressure lowering activity.

A further class of chromans, and their corresponding chromenes, has now been discovered which are characterised by the presence of an aminoalkylamido, aminoalkyl-thioamido, ureido, thioureido, optionally esterified hydroxyamido or hydroxythioamido, or carbamoylamido or optionally esterified carboxyamido group that substitutes the chroman or chromene in the 4-position. In addition, such chromans and chromenes have been found to have blood pressure lowering activity.

Accordingly, the present invention provides a compound of formula (I):

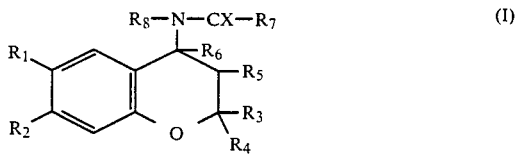

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is selected from the class consisting of $C_{1-6}$ alkyl substituted by amino optionally substituted by one or two $C_{1-6}$ alkyl groups which may be the same or different; amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen; or $C_{1-6}$ alkoxy, or phenoxy optionally substituted by $C_{1-6}$ alkyl, $C_{1-6}$ alkoxy or halogen; or, when X is oxygen, $R_7$ is further selected from the class of carboxy, $C_{1-6}$ alkoxycarbonyl, or aminocarbonyl optionally substituted by one or two $C_{1-6}$ alkyl groups which may be the same or different;
$R_8$ is hydrogen or $C_{1-6}$ alkyl; and
X is oxygen or sulphur;
the $R_8$-N-CX-$R_7$ group being trans to the $R_5$ group when $R_5$ and $R_6$ together are not a bond:
or, when the compound of formula (I) contains a salifiable group, a pharmaceutically acceptable salt thereof.

When one of $R_1$ and $R_2$ is hydrogen, the other is preferably selected from the class of $C_{1-6}$ alkylcarbonyl, $C_{1-6}$ alkoxycarbonyl, nitro or cyano. In particular, when one of $R_1$ and $R_2$ is hydrogen, the other is preferably nitro, cyano or acetyl.

When one of $R_1$ and $R_2$ is hydrogen, it is preferred that $R_2$ is hydrogen.

When one of $R_1$ and $R_2$ is nitro, cyano or $C_{1-3}$ alkylcarbonyl, and the other is methoxy or amino optionally substituted as hereinbefore defined, the other is preferably amino optionally substituted by one or two $C_{1-6}$ alkyl groups or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro or cyano or $C_{1-3}$ aklylcarbonyl, such as acetyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy. However, it is preferred that $R_5$ and $R_6$ together are a bond, or, in particular, that $R_5$ is hydroxy and $R_6$ is hydrogen.

Examples of $R_7$ include the following groups:

A group $(CH_2)_n NR_9 R_{10}$ where n is 1 to 6, and $R_9$ and $R_{10}$ are each independently hydrogen or $C_{1-6}$ alkyl. Examples of n include 1 and 2, in particular 1. Preferably $R_9$ and $R_{10}$ are each independently selected from hydrogen and methyl.

Amino optionally substituted by a methyl, ethyl, propyl, butyl, allyl or trichloroacetyl group or by a phenyl group optionally substituted by one methyl, methoxy or chloro group or atom, in particular amino, methylamino, and phenylamino optionally substituted in the phenyl ring by one methyl, methoxy or chloro group or atom.

Methoxy, ethoxy, n- and iso-propoxy, and phenoxy optionally substituted by one methyl, ethyl, methoxy, ethoxy, chloro or bromo group or atom, preferably methoxy, ethoxy, and phenoxy optionally substituted by one methyl, methoxy or chloro group or atom, in particular ethoxy, X is preferably oxygen in this case.

When X is oxygen: carboxyl, methoxycarbonyl, ethoxycarbonyl, aminocarbonyl, methylaminocarbonyl and dimethylaminocarbonyl. in particular ethoxycarbonyl.

Examples of $R_8$ include hydrogen, methyl, ethyl, n- or iso-propyl. Preferably, $R_8$ is hydrogen or methyl, especially hydrogen.

Examples of a pharmaceutically acceptable salt of a compound of formula (I), when the compound of formula (I) contains a salifiable group which is an optionally substituted amino group, include acid addition salts such as the hydrochloride and hydrobromide salts. Such a group may be an $R_1$ or $R_2$ group or be within an $R_7$ group. An $R_7$ carboxy group may also be salified to form metal salts such as alkali metal salts, or optionally substituted ammonium salts.

Preferably, a compound of formula (I) is in substantially pure form.

The compounds of formula (I) wherein $R_5$ is hydrogen, hydroxy, $C_{1-6}$ alkoxy or $C_{1-7}$ acyloxy and $R_6$ is hydrogen have a least one asymmetric center and, therefore, can exist as enantiomers. The present invention extends to all such isomers individually and as racemates.

Examples of compounds of formula (I) include the compounds prepared in the Examples hereinafter.

A group of compounds of formula (I) is those wherein $R_7$ is a group $(CH_2)_n NR_9 R_{10}$ where n, $R_9$ and $R_{10}$ are as hereinbefore defined.

A second group of compounds of formula (I) is those wherein $R_7$ is amino optionally substituted by a $C_{1-6}$ alkyl group, or by a phenyl group optionally substituted by $C_{1-6}$ alkyl, $C_{1-6}$ alkoxy or halogen.

A third group of compounds of formula (I) is those wherein $R_7$ is $C_{1-6}$ alkoxy, or phenoxy optionally substituted by $C_{1-6}$ alkyl, $C_{1-6}$ alkoxy or halogen.

A fourth group of compounds of formula (I) is those wherein X is oxygen and $R_7$ is carboxy, $C_{1-6}$ alkoxycarbonyl, or aminocarbonyl optionally substituted by one or two $C_{1-6}$ alkyl groups.

The present invention also provides a process for preparing a compound of formula (I), which comprises acylating a compound of formula (II):

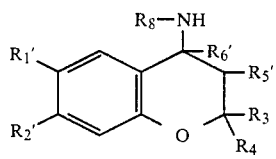

(II)

wherein $R_1'$ and $R_2'$ are $R_1$ and $R_2$, as defined hereinbefore, or a group or atom convertible thereto, $R_3$, $R_4$ and $R_8$ are as defined hereinbefore, $R_5'$ is hydrogen, hydroxy, $C_{1-6}$ alkoxy or $C_{1-7}$ acyloxy and $R_6'$ is hydrogen, the $R_8 NH$ group being trans to the $R_5'$ group (i) with an acylating agent of formula (III):

 (III)

wherein $R_7'$ is $R_7$ other than amino optionally substituted as hereinbefore defined, carboxy or aminocarbonyl optionally substituted as hereinbefore defined, or a group convertible thereto; and $L_1$ is a leaving group, and thereafter in the case where $R_7'$ is a group convertible to $R_7$ which is other than amino optionally substituted as hereinbefore defined, carboxy or aminocarbonyl optionally substituted as hereinbefore defined, converting $R_7'$ to other $R_7$ which is also other than amino optionally substituted as hereinbefore defined, carboxy or aminocarbonyl optionally substituted as hereinbefore defined; in the case where $R_7'$ in the resulting compound is $C_{1-6}$ alkoxycarbonyl optionally converting $R_7'$ to $R_7$ carboxy or aminocarbonyl optionally substituted as hereinbefore defined; or (ii) with a compound of formula (IV)

 (IV)

wherein $R_{11}$ is hydrogen, $C_{1-6}$ alkyl, $C_{1-6}$ alkenyl, $C_{1-6}$ alkanoyl optionally substituted by up to three halo atoms, or phenyl optionally substituted by $C_{1-6}$ alkyl, $C_{1-6}$ alkoxy or halogen; and X is oxygen or sulphur, and thereafter when $R_{11}$ is hydrogen, optionally converting $R_{11}$; and thereafter in the case where $R_1'$ or $R_2'$ is a group or atom convertible into $R_1$ or $R_2$, converting the group or atom into $R_1$ or $R_2$; optionally converting $R_1$, $R_2$ or $R_5$ in the resulting compound of formula (I) into another $R_1$, $R_2$ or $R_5$;

in the case where $R_5$ and $R_6$ in the resulting compound are hydroxy and hydrogen respectively, optionally dehydrating the compound to give a compound wherein $R_5$ and $R_6$ together are a bond; in the case where $R_5$ and $R_6$ together are a bond in the resulting compound, optionally reducing the compound to give a compound wherein $R_5$ and $R_6$ are each hydrogen; and optionally thiating the carbonyl group of any $R_8 NCOR_7$ group in the resulting compound of formula (I) where $R_7$ is other than carboxy, $C_{1-6}$ alkoxycarbonyl or aminocarbonyl optionally substituted as hereinbefore defined to give another compound of formula (I), wherein X is sulphur; and, when the resulting compound of formula (I) containing a salifiable group, optionally forming a pharmaceutically acceptable salt thereof.

In process variant (i), when $R_7'$ is $C_{1-6}$ alkyl substituted by optionally substituted amino as hereinbefore defined, or a group convertible thereto, the leaving group $L_1$ is a group that is displaceable by a primary or secondary amino nucleophile. Examples of such a group include $C_{2-9}$ acyloxy, such as $C_{1-4}$ alkylcarbonyloxy, and, preferably halogen, such as chloro and bromo. When the leaving group $L_1$ is either of these examples, the acylating agent of formula (III) is either an acid anhydride or an acid halide. When it is acid anhydride, it may be a mixed or simple anhydride. If it is a mixed anhydride, it may be prepared in situ from a carboxylic acid and an acid halide, although this is much less preferred than using the halide itself. A further example of the leaving group $L_1$ is a hydroxy group although this is less preferred than the leaving groups previously mentioned.

In process variant (i), when $R_7$ in the desired compound of formula (I) is an $R_7$ substituted alkyl group as hereinbefore defined it is preferred that $R_7$ is a group convertible to the $R_7$ substituted alkyl group as hereinbefore defined in particular that it is $C_{1-6}$ alkyl substituted by halo, especially bromo. The $R_7'$ halo substituent in the resultant compound of process variant (i) may be converted to an $R_7$ substituent which is amino optionally substituted as hereinbefore defined by a conventionaly amination reaction with ammonia or a corresponding alkyl- or dialkylamine.

Less favourably $R_7'$ may be $C_{1-6}$ alkyl substituted by protected amino, protected $C_{1-6}$ alkyl amino or amino substituted by two independent $C_{1-6}$ alkyl groups, it being necessary to protect the $R_7$ amino function in process variant (i). Particular examples of such a group $R_7'$ include a group $(CU_2)_n NR_9'R_{10}'$ where n is 1 to 6, and $R_9'$ and $R_{10}'$ together are a divalent protecting group, one of $R_9'$ and $R_{10}'$ is methyl and the other is a monovalent protecting group, on each of $R_9'$ and $R_{10}'$ is methyl. Suitable protecting groups and deprotection conditions to achieve the subsequent $R_7'$ to $R_7$ conversion without breaking the $R_8.N.CO.R_7$ amide bond will be readily apparent to the skilled man.

When the acylating agent of formula (III) is an acid anhydride, the acylation of the compound of formula (II) is, preferably, carried out using the anhydride as the solvent in the presence of an acid acceptor, such as sodium acetate, or, preferably, triethylamine.

When the acylating agent of formula (III) is an acid halide, the acylation of the compound of formula (II) is, preferably, carried out in a medium, such as chloroform or dichloromethane, in the presence of an acid acceptor, such as triethylamine, trimethylamine, pyridine, picoline or calcium, potassium or sodium carbonate.

In process variant (i), when $R_7'$ is $C_{1-6}$ alkoxy, phenoxy optionally substituted as hereinbefore defined, or $C_{1-6}$ alkoxycarbonyl, examples of the leaving group $L_1$ include halogen such as chloro or bromo. Acylation is then preferably carried out under the reaction conditions described hereinbefore for corresponding $L_1$ groups.

When $R_5'$ in a compound of formula (II) in process variant (i) is hydroxy, there is a risk of a side-reaction between the hydroxy group and the acylating agent of formula (III), but this may be minimised by effecting the reaction at relatively low temperatures, e.g. at below 10° C. Alternatively, $R_5'$ may be $C_{1-7}$ acyloxy in a compound of formula (II) and, after reaction with the acylating agent of formula (III), be converted into hydroxy, as described hereinafter. It is however, preferred that the reaction is controlled conventionally as described hereinbefore, such that only the amine, $R_8NH$-, is acylated.

In process variant (ii), when $R_{11}$ is a compound of formula (IV) is $C_{1-6}$ alkyl, $C_{1-6}$ alkanoyl optionally substituted as hereinbefore defined, or phenyl optionally substituted as hereinbefore defined, the reaction between the compounds of formulae (II) and (IV) is, preferably, carried out in a solvent, such as methylene chloride, at below room temperature, in particular below 10° C.

When $R_{11}$ is hydrogen, the reaction between the compounds of formulae (II) and (IV) is, preferably, carried out using a corresponding alkali metal cyanate or thiocyanate, for example that of sodium or potassium, in an aqueous medium (optionally methanolic) acidified with a mineral acid, such as dilute hydrochloric acid. A slightly elevated temperature such as 50° to 90° C. is apt.

Conversions of an aromatic group into $R_1$ or $R_2$, as defined hereinbefore, are generally known in the art of aromatic chemistry. For example, it is preferred when carrying out the acylation of a compound of formula (II), first to protect any unsubstituted amino group, that may be present for $R_1$ or $R_2$, and afterwards to convert the protected amino moiety into the required amino group. Examples of protecting agents include acyl groups, such as acetyl, which may be added and removed conventionally. If it is desired to protect an amino moiety in the presence of a cyano group then a more appropriate method is to use a trifluoroacetyl protecting group which may be removed by mild hydrolysis or to use a benzyloxycarbonyl or a p-nitrobenzyloxycarbonyl protecting group which may be removed by mild catalytic hydrogenolysis.

If the optional thiation reaction is to be carried out in order to obtain a compound of formula (I), wherein one or the other of $R_1$ and $R_2$ is a carbonyl-containing group and X is sulphur, it is preferred to use in the acylation reaction the corresponding compound of formula (II), wherein $R_1'$ or $R_2'$ is a protected carbonyl-containing group, and after thiation to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Examples of an optional conversion of $R_1$ or $R_2$ in the resulting compound of formula (I) into another $R_1$ or $R_2$, as defined hereinbefore, include the optional conversion of an α-hydroxyethyl group into acetyl by oxidation, the optional conversion of an amino group into a chlorine atom by the Sandmeyer reaction the optional conversion of an amino group into an amino group substituted by one or two $C_{1-6}$ alkyl or by $C_{2-7}$ alkanoyl, or the optional conversion of a hydrogen atom into a nitro group by nitration.

Examples of an optional conversion of $R_5$ in a compound of formula (I) into another $R_5$ are generally known in the art. For example, when $R_5$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of a base such such as triethylamine. Alternatively, when $R_5$ is $C_{2-7}$ acyloxy or it may be converted into hydroxy by conventional hydrolysis with for example, dilute mineral acid.

The optional dehydration of a resulting compound of formula (I), wherein $R_5$ and $R_6$ are hydroxy and hydrogen respectively, into another compound of formula (I), wherein $R_5$ and $R_6$ together are a bond, may be carried out in accordance with conventional dehydration conditions, for example, by using a dehydrating agent, such as sodium hydride, in an inert solvent, such as dry tetrahydrofuran, at reflux temperature.

The optional reduction of an $R_5$-$R_6$ bond may be effected by conventional catalytic hydrogenation for example using palladium on charcoal.

The optional conversion of a resultant compound of process variant (i) wherein $R_7'$ is $C_{1-6}$ alkoxycarbonyl, into a compound of formula (I), wherein $R_7$ is carboxy or aminocarbonyl optionally substituted as hereinbefore defined may be carried out conventionally. For example, the optional conversion into a compound of formula (I), wherein $R_7$ is carboxy, may be carried out by hydrolysis. The resulting compound of formula (I), wherein $R_7$ is carboxy may then be optionally converted into another compound of formula (I), wherein $R_7$ is aminocarbonyl optionally substituted as hereinbefore defined, by first forming the acid halide, such as the chloride, and then reacting the acid halide with ammonia optionally substituted by one or two $C_{1-6}$ alkyl groups which may be the same or different.

The optional thiation of the $R_8$-N-CO-$R_7$ group in a compound of formula (I) where $R_7$ is other than carboxy, $C_{1-6}$ alkoxycarbonyl or aminocarbonyl optionally substituted as hereinbefore defined to give another compound of formula (I), wherin X is sulphur, is, preferably, carried out with conventional thiation agents, such as hydrogen sulphide, phosporous pentasulphide and Lawesson's reagent (p-methoxyphenylthiophosphine sulphide dimer). The use of hydrogen sulphide or phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

The optional formation of a pharmaceutically acceptable salt, when the resulting compound of formula (I) contains a salifiable group may be carried out conventionally.

A compound of formula (II) may be prepared by reacting a compound of formula (V):

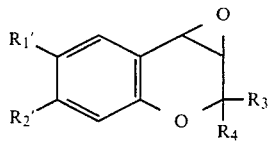

(V)

wherein $R_1'$, $R_2'$, $R_3$ and $R_4$ are as defined hereinbefore, with a compound of formula (VI):

$R_8NH_2$      (VI)

wherein $R_8$ is as defined hereinbefore; and optionally converting the hydroxy group for $R_5'$ in the resulting compound of formula (II) into a $C_{1-6}$ alkoxy or $C_{1-7}$ acyloxy group.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_5'$ in the resulting compound of formula (II) into a $C_{1-6}$ alkoxy or $C_{1-7}$ acyloxy group may be carried out as described hereinbefore in relation to the corresponding conversion of $R_5$ in a compound of formula (I).

A compound of formula (VI) may be prepared, preferably in situ, by reacting a compound of formula (VII):

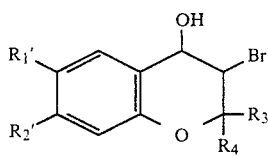

(VII)

wherein $R_1'$, $R_2'$, $R_3$ and $R_4$ are as defined hereinbefore and the hydroxy group is trans to the bromo atom, with a base, such as potassium hydroxide, in a solvent, such as ether or aqueous dioxan.

Compounds of formula (VII) are known and may be prepared in accordance with any appropriate known process, for example, by the process described in the aforementioned U.S. patents and European patent publications. Schematically, such process can be depicted thus.

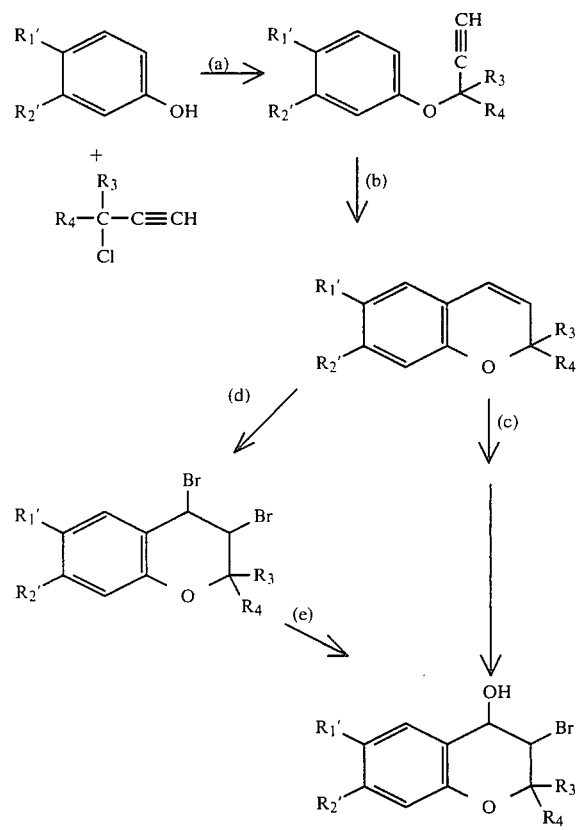

(a) Room temperature; NaOH/40% benzyltrimethyl-ammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

As mentioned previously, the compounds of formula (I) exist in optically active forms, and the processes of the present invention produce mixtures of such forms. The individual isomers may be separated one from the other by chromatography using a chiral phase.

It is preferred that the compounds of formula (I) are isolated in substantially pure form.

The compounds of formula (V) to (VII) are also known or can be prepared analogously to the preparation of known compounds, or are routinely derivable from known compounds.

As mentioned previously, the compounds of formula (I) have been found to have blood-pressure lowering activity. They are therefore useful in the treatment of hypertension.

The present invention accordingly provides a pharmaceutical composition which comprises a compound of formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof and a pharmaceutically acceptable carrier.

The compositions are preferably adapted for oral administration. However, they may be adapted for other modes of administration, for example parenteral administration for patients suffering from heart failure.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The present invention further provides a compound of formula (I) or a pharmaceutically acceptable salt thereof for use in the treatment or prophylaxis of maladies in mammals, in particular of hypertension.

The following examples relate to the preparation of compounds of formula (I).

All temperatures therein are in °C.

EXAMPLE 1

Trans-6-cyano-3,4-dihydro-2,2-dimethyl-4-(methylaminomethylenecarbonylamino)-2H-1-benzopyran-3-ol (E1)

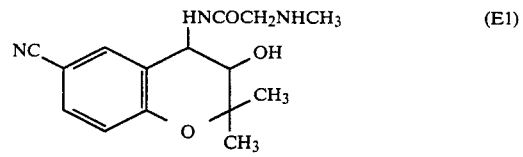

Trans-4-(chloroacetylamino)-6-cyano-3,4-dihydro-2,2-dimethyl-2H-1-benzopyran-3-ol (0.25 g, prepared as described in European Patent Application No. 95,316A) and 40% aqueous methylamine solution (5 ml) were dissolved in ethanol (10 ml) at room temperature. After 3 hours, the solution was evaporated taken up in ethyl acetate, washed with water and dried over anhydrous magnesium sulphate. Filtration and evaporation and recrystallisation from ethyl acetate gave the title compound (0.12 g), mp 159°–160.5° C.

NMR (CD$_3$OD) δ 1.28 (3H,s), 1.50 (3H,s), 2.46 (3H,s), 3.37 (2H,s), 3.56 (1H,d,J=10 Hz), 5.03 (1H,d,J=10 Hz), 6.92 (1H,d,J=9 Hz), 7.50 (2H,m).

Similarly prepared are trans-4-(aminomethylenecarbonylamino)-6-cyano-3,6-dihydro-2,3-dimethyl-2H-1-benzopyran-3-ol (E12) and trans-6-cyano-3,4-dihydro-2,2-dimethyl-4-(dimethylaminomethylenecarbonylamino)-2H-1-benzopyran-3-ol (E13).

EXAMPLE 2

Trans-6-Cyano-3,4-dihydro-2,2-dimethyl-4-(N-methylureido)-2H-1-benzopyran-3-ol (E2)

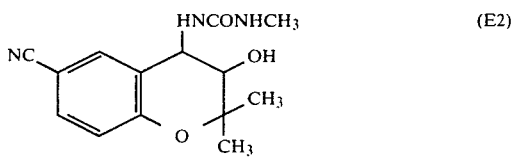

Trans-4-amino-6-cyano-3,4-dihydro-2,2-dimethyl-2H-1-benzopyran-3-ol (2.00 g) in dichloromethane (30 ml) was added dropwise to a stirred solution of methyl isocyanate (0.54 ml) in dichloromethane (15 ml), the temperature being maintained at below 10° C. After 15 min a white precipitate formed and the reaction mixture was allowed to reach room temperature. The solid was filtered and recrystallised from dichloromethane to give the title compound (1.30 g) as crystals of m.p. 143°–146° C.

NMR (DCDl$_3$) δ 1.25 (3H,s), 1.46 (3H,s), 2.73 (3H,d,J=5 Hz) collapsing to singlet on addition of D$_2$O, 3.56 (1H,d,J=9 Hz), 4.75 (1H,t,J=9 Hz) collapsing to doublet J=9 on addition of D$_2$O, 5.01 (1H,s,exchangeable), 5.40–5.75 (2H,m,exchangeable), 6.85 (1H,d,J=8 Hz), 7.40 (1H,q,J=8,2 Hz), 7.15 (1H,irreg s).

The starting material was prepared in accordance with the procedure described in European Patent Publication No. 76 075.

EXAMPLE 3

6-Cyano-3,4-dihydro-2,2-dimethyl-trans-4-(N-phenylureido)-2H-1-benzopyran-3-ol (E3)

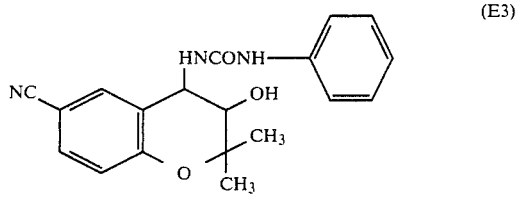

To trans-4-amino-3,4-dihydro-2,2-dimethyl-2H-benzo[b]pyran-3-ol (2.0 g) dissolved in ice cooled dichloromethane (25 ml), was added phenylisocyanate (1 ml) in dichloromethane (15 ml). The title compound, a white solid, precipitated out, and this was collected by filtration, and dried (2.6 g). m.p. 226°–227° C.

NMR (CDCl$_3$/CD$_3$OD) δ 1.30 (3H,s), 1.50 (3H,s), 3.60 (1H,d,J=10 Hz), 4.88 (1H,d,J=10 Hz), 6.87 (1H,d,J=9 Hz), 6.97–7.75 (7H, series of m).

EXAMPLE 4

Trans-4-(N-butylureido)-6-cyano-3,4-dihydro-2,2-dimethyl-2H-1-benzopyran-3-ol (E4)

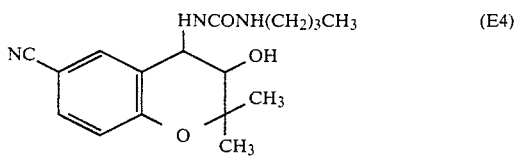

To trans-4-amino-6-cyano-3,4-dihydro-2,2-dimethyl-2H-1-benzopyran-3-ol (1.00 g) in dichloromethane (40 ml) cooled in an ice bath was added butylisocyanate (0.25 ml) in dichloromethane. The solution was stirred for 30 min and a white precipitate formed. This precipitate was collected and dried (1.12 g) and identified as the title compound;

mp 173°–174° C.

NMR (CDCl$_3$) δ 1.00 (3H,irreg d,J-8 Hz), 1.27 (3H,s) and 1.50 (3H,s) overlapping 1.25–1.65 (4H,m), 3.20 (2H,irreg t,J=8,8 Hz), 3.57 (1H,d,J=9 Hz), 4.70–5.30 (3H,m) collapsing to 4.83 (1H,d,J=9 Hz) on addition of D$_2$O, 6.87 (1H,d,J=9 Hz), 7.43 (1H,q,J=9,2 Hz), 7.68 (1H,narrow m).

Trans-4-cyano-3,4-dihydro-2,2-dimethyl-4-(N-n-propylureido)-2H-1-benzopyran (E14) is prepared in an analogous manner.

EXAMPLE 5

Trans-6-cyano-4-(ethyl oxalamido)-3,4-dihydro-2,2-dimethyl-2H-1-benzopyran-3-ol (E5)

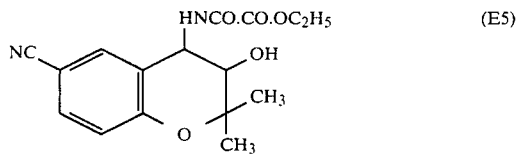

To a mixture of trans-4-amino-6-cyano-3,4-dihydro-2,2-dimethyl-2H-benzo[b]pyran-3-ol (872 mg) and triethylamine (0.64 ml) in ice cooled dichloromethane (20 ml) was added ethyl oxalyl chloride (0.56 ml). After 1 hour the solution was allowed to attain room temperature. It was washed with water and brine and dried over magnesium sulphate. Filtration and evaporation gave a solid which was recrystallised from ethyl acetate-pentane to give the title compound (640 mg) as crystals of m.p. 160°–162° C.

NMR (CDCl$_3$+D$_2$O) δ 1.31 (3H,s), 1.41 (3H,t,J=7,7 Hz), 1.53 (3H,s), 3.77 (1H,d,J=10 Hz), 4.38 (2H,q,J=7,7,7 Hz), 5.10 (1H,d,J=10 Hz), 6.91 (1H,d,J=9 Hz), 7.40–7.65 (2H,m).

EXAMPLE 6

Trans-6-cyano-3,4-dihydro-2,2-dimethyl-4-(N-methylthiureido)-2H-1-benzopyran-3-ol (E6)

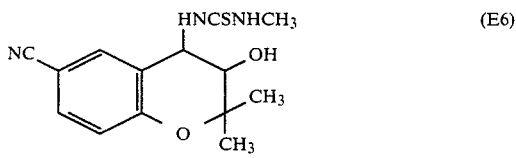

Methyl isothiocyanate (0.34 g) in dichloromethane (10 ml) was added to trans-4-amino-6-cyano-3,4-dihydro-2,2-dimethyl-2H-1-benzopyran-3-ol (1.00 g) stirred in dichloromethane (30 ml) at below 10° C. The reaction was stirred for 66 hours at room temperature. The solid which precipitated out was filtered (0.7 g) and identified as the title thiureide mp 203°–205° C.

Mass spectrum M+-H$_2$O at M/Z 273.0934 Calcd for C$_{14}$H$_{15}$N$_3$OS 273.0936.

EXAMPLE 7

Trans-4-(N-allylthioureido)-6-cyano-3,4-dihydro-2,2-dimethyl-2H-benzopyran-3-ol (E7)

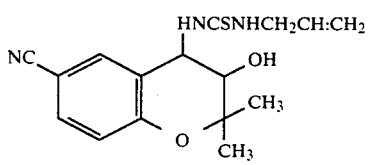 (E7)

This compound was made in an analogous manner to the compound of (E6), allylisothiocyanate being employed, and the reaction time 19 hr. The title compound had mp 177°–178° C.

Mass spectrum M+ at M/Z 317.1199 Calcd for $C_{16}H_{19}N_3O_2S$ 317.1198.

EXAMPLE 8

Trans-6-acetyl-3,4-dihydro-2,2-dimethyl-4-(N-methylthioureido)-2H-1-benzopyran-3-ol (E8)

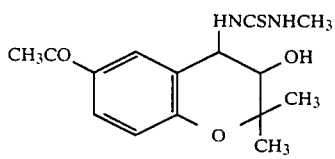 (E8)

The compound of example 8 was prepared in an analogous manner to the compound of (E6), employing trans-6-acetyl-4-amino-3,4-dihydro-2,2-dimethyl-2H-1-benzopyran-3-ol as starting material. The title compound was recrystallised from ethyl acetate-pentane; mp 203°–204° C.

NMR (CDCl$_3$+CD$_3$OD) δ 1.34 (3H,s), 1.51 (3H,s), 2.06 (3H,s), 3.10 (3H,s), 3.66 (1H,d,J=9 Hz), 5.67 (1H,d,J=9 Hz), 6.86 (1H,d,J=9 Hz), 7.80 (1H,q,J=9,2 Hz), 7.94 (1H,narrow m).

EXAMPLE 9

Trans-6-cyano-4-(trichloroacetylureido)-3,4-dihydro-2,2-dimethyl-2H-1-benzopyran-3-ol (E9)

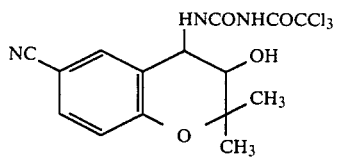 (E9)

The compound of this example was prepared in an analogous manner to the compound of (E2) using trichloroacetyl isocyanate. The title compound was isolated from the reaction mixture by filtration: mp 231°–233° C.

NMR (CD$_3$OD) δ 1.27 (3H,s), 1.49 (3H,s), 3.79 (1H,d,J=9 Hz), 4.94 (1H,d,J=9 Hz), 6.91 (1H,d,J=8 Hz), 7.51 (1H,q,J=8,2 Hz), 7.61 (1H,narrow m).

EXAMPLE 10

Trans-6-cyano-4-(ethoxycarbonylamino)-3,4-dihydro-2,2-dimethyl-2H-1-benzopyran-3-ol (E10)

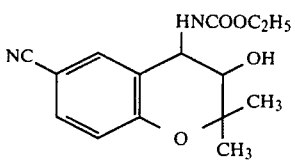 (E10)

To trans-4-amino-6-cyano-3,4-dihydro-2,2-dimethyl-2H-1-benzopyran-3-ol (1.09 g) and triethylamine (0.77 ml) in dichloromethane (20 ml), cooled in an ice bath, was added ethylchloroformate (0.67 ml). The mixture was allowed to attain room temperature and stirred for 2 days. The reaction mixture was washed with water and dried over anhydrous magnesium sulphate. Filtration and evaporation and chromatography (chromatotron, gradient elution: 10–30% Ethyl acetate-pentane) gave one fraction (456 mg) which was recrystallised from ethyl acetate-pentane to give the compound of this example (319 mg); mp 147°–148° C.

NMR (CDCl$_3$) δ 1.26 (3H,s) overlapping, 1.28 (3H,t,J=7, Hz), 1.44 (3H,s), 3.53 (1H,d,J=8 Hz) overlapping, 3.65 (1H,m), 4.13 (2H,q,J=7 Hz), 4.68 (1H,t,J=7 Hz), 5.18 (1H,d,J=7 Hz), 6.77 (1H,d,J=8 Hz), 7.35 (1H,q,J=8,2 Hz), 7.50 (1H,narrow m).

EXAMPLE 11

Trans-6-cyano-3,4-dihydro-2,2-dimethyl-4-(N-ureido)-2H-1-benzopyran-3-ol (E11)

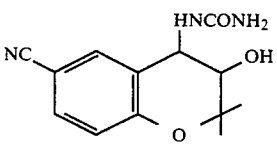 (E11)

To a stirred suspension of 6-cyano-3,4-dihydro-epoxy-2H-benzo[b]pyran (1.0 g) in water (30 mls) at 0° C. was added 5N hydrochloric acid (0.92 mls). After warming to 70° C., methanol (3 mls) was added to give a homogeneous solution and sodium cyanate (0.3 g) added. After 2½ hours the reaction was allowed to cool and crystallise. The resulting solid was filtered off, chromatographed, and recrystallised to give the title compound as crystals of m.p. 212°–214° C.

NMR (CO$_3$OD) δ 1.29 (3H, s), 1.51 (3H, s), 3.55 (1H, d, J=9 Hz), 4.79 (1H, d, J=9 Hz), 6.88 (1H, d, J=9 Hz), 7.48 (1H, q, J=9,2 Hz), 7.70 (1H, narrow m).

PHARMACOLOGICAL DATA—ANTIHYPERTENSIVE ACTIVITY

Systolic blood pressures were recorded by a modification of the tail cuff method described by I. M. Claxton, M. G. Palfreyman, R. H. Poyser, R. L. Whiting, European Journal of Pharmacology, 37, 179 (1976).

W+W BP recorder, model 8005, was used to display pulses. Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| | Time Post Dose Hours | % Change in Systolic Blood | % Change in Heart Rate |
|---|---|---|---|
| Compound (E2) | | | |
| 6 rats | 1 | −51 ± 5* | 8 ± 6 |
| Dose 1 mg/kg p.o. | 2 | −57 ± 3 | 7 ± 2 |
| Initial Blood Pressure | 4 | −61 ± 3* | 12 ± 3 |
| 256 ± 4 mmHg Initial Heart Rate | 6 | −52 ± 4 | 11 ± 3 |
| 441 ± 9 beats/min | | | |

*1 rat had no measurable pulse

| | | | |
|---|---|---|---|
| Compound (E6) | | | |
| 6 rats | 1* | −31 ± 2 | 6 ± 3 |
| Dose 3 mg/kg p.o. | 2* | −33 ± 3 | −2 ± 2 |
| Initial Blood Pressure | 4** | −22 | 4 |
| 212 ± 5 mmHg Initial Heart Rate | 6*** | −13 ± 6 | −7 ± 2 |
| 503 ± 11 beats/min | | | |

*2 rats had no measurable pulse
**3 rats had no measurable pulse
***1 rat had no measurable pulse

| | | | |
|---|---|---|---|
| Compound (E9) | | | |
| 6 rats | 1 | −22 ± 3 | −1 ± 2 |
| Dose 10 mg/kg p.o. | 2 | −28 ± 2 | −1 ± 3 |
| Initial Blood Pressure | 4* | −26 ± 2 | −5 ± 3 |
| 213 ± 7 mmHg Initial Heart Rate | 6 | −15 ± 2 | −3 ± 3 |
| 485 ± 7 beats/min | | | |

*1 rat had no measurable pulse

| | | | |
|---|---|---|---|
| Compound (E10) | | | |
| 6 rats | 1* | −54 ± 3 | −3 ± 4 |
| Dose 10 mg/kg p.o. | 2** | −40 ± 3 | −1 ± 3 |
| Initial Blood Pressure | 4*** | −33 ± 0 | −8 ± 3 |
| 245 ± 5 mmHg Initial Heart Rate | 6* | −30 ± 4 | −11 ± 3 |
| 454 ± 15 beats/min | | | |

*2 rats had no measurable pulse
**1 rat had no measurable pulse
***3 rats had no measurable pulse

We claim:

1. A compound of formula (I):

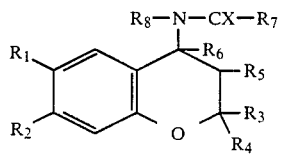

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ carboxylic acyloxy and $R_6$ is hydrogen or $R_5$ and $R_6$ together are a bond;
$R_7$ is selected from the class consisting of $C_{1-6}$ alkyl substituted by amino optionally substituted by one or two $C_{1-6}$ alkyl groups which may be the same or different; amino optionally substituted by a $C_{1-6}$ alkyl or $C_{1-6}$ alkenyl group or a $C_{1-6}$ alkanoyl group optionally substituted by up to three halo atoms or by a phenyl group optionally substituted by $C_{1-6}$ alkyl, $C_{1-6}$ alkoxy or halogen; or $C_{1-6}$ alkoxy, or phenoxy optionally substituted by $C_{1-6}$ alkyl, $C_{1-6}$ alkoxy or halogen; or, when X is oxygen, $R_7$ is further selected from the class of carboxy, $C_{1-6}$ alkoxycarbonyl, or aminocarbonyl optionally substituted by one or two $C_{1-6}$ alkyl groups which may be the same or different;
$R_8$ is hydrogen or $C_{1-6}$ alkyl; and
X is oxygen or sulphur;
the $R_8$-N-CX-$R_7$ group being trans to the $R_5$ group when $R_5$ and $R_6$ together are not a bond;
or, when the compound of formula (I) contains a salifiable group, a pharmaceutically acceptable salt thereof.

2. A compound according to claim 1 wherein $R_7$ is a group $(CH_2)_nNR_9R_{10}$ where n is 1 to 6, and $R_9$ and $R_{10}$ are each independently hydrogen or $C_{1-6}$ alkyl.

3. A compound according to claim 1 wherein $R_7$ is amino optionally substituted by a $C_{1-6}$ alkyl group, or by a phenyl group optionally substituted by $C_{1-6}$ alkyl, $C_{1-6}$ alkoxy or halogen.

4. A compound according to claim 1 wherein $R_7$ is $C_{1-6}$ alkoxy, or phenoxy optionally substituted by $C_{1-6}$ alkyl, $C_{1-6}$ alkoxy or halogen.

5. A compound according to claim 1 wherein X is oxygen and $R_7$ is carboxy, $C_{1-6}$ alkoxycarbonyl, or aminocarbonyl optionally substituted by one or two $C_{1-6}$ alkyl groups.

6. A compound according to claim 1, wherein $R_1$ is nitro, cyano or acetyl, and $R_2$ is hydrogen.

7. A compound which is trans-6-cyano-3,4-dihydro-2,2-dimethyl-4-(N-methylureido)-2H-1-benzopyran-3-ol, trans-6-cyano-3,4-dihydro-2,2-dimethyl-4-(N-methylthiureido)-2H-1-benzopyran-3-ol, trans-6-cyano-4-(trichloroacetylureido)-3,4-dihydro-2,2-dimethyl-2H-1-benzopyran-3-ol, or trans-6-cyano-4-(ethoxycarbonylamino)-3,4-dihydro-2,2-dimethyl-2H-1-benzopyran-3-ol.

8. An anti-hypertensive pharmaceutical composition which comprises an anti-hypertensive effective amount of a compound according to claim 1 of formula (I) or a pharmaceutically acceptable salt thereof and a pharmaceutically acceptable carrier.

9. A method of prophylaxis or treatment of hypertension in mammals including man, which comprises administering to the suffering mammal an anti-hypertensive affective amount of a compound according to claim 1 of formula (I) or a pharmaceutically acceptable salt thereof.

10. A compound according to claim 2, wherein $R_1$ is nitro, cyano or acetyl, and $R_2$ is hydrogen.

11. A compound according to claim 3, wherein $R_1$ is nitro, cyano or acetyl, and $R_2$ is hydrogen.

12. A compound according to claim 4, wherein $R_1$ is nitro, cyano or acetyl, and $R_2$ is hydrogen.

13. A compound according to claim 5, wherein $R_1$ is nitro, cyano or acetyl, and $R_2$ is hydrogen.

14. A compound according to claim 1, which is trans-6-cyano-3,4-dihydro-2,2-dimethyl-4-(N-methylureido)-2H-1-benzopyran-3-ol.

15. A compound according to claim 1, which is trans-6-cyano-3,4-dihydro-2,2-dimethyl-4-(methylaminomethylenecarbonylamino)-2H-1-benzopyran-3-ol, 6-cyano-3,4-dihydro-2,2-dimethyl-trans-4-(N-phenylureido)-2H-1-benzopyran-3-ol, trans-4-(N-butylureido)-6-cyano-3,4-dihydro-2,2-dimethyl-2H-1-benzopyran-3-ol, trans-6-cyano-4-(ethyl oxalamido)-3,4-dihydro-2,2-dimethyl-2H-1-benzopyran-3-ol, trans-4-(N-allylthiureido)-6-cyano-3,4-dihydro-2,2-dimethyl-2H-benzopyran-3-ol, trans-6-acetyl-3,4-dihydro-2,2-dimethyl-4-(N-methylthiureido)-2H-1-benzopyran-3-ol, or trans-6-cyano-3,4-dihydro-2,2-dimethyl-4-(N-ureido)-2H-1-benzopyran-3-ol.

* * * * *